US00PP25852P2

(12) United States Plant Patent
Farrow

(10) Patent No.: US PP25,852 P2
(45) Date of Patent: Sep. 1, 2015

(54) ***ILEX* PLANT NAMED 'FARROWSK6'**

(50) Latin Name: *Ilex crenata*
Varietal Denomination: FarrowSK6

(71) Applicant: Michael W. Farrow, Earleville, MD (US)

(72) Inventor: Michael W. Farrow, Earleville, MD (US)

(73) Assignee: Spring Meadow Nursurey Inc., Grand Haven, MI (US)

( * ) Notice: Subject to any disclaimer, the term of this patent is extended or adjusted under 35 U.S.C. 154(b) by 89 days.

(21) Appl. No.: 13/998,229

(22) Filed: Oct. 11, 2013

(51) Int. Cl.
*A01H 5/00* (2006.01)

(52) U.S. Cl.
USPC ..... Plt./247

(58) Field of Classification Search
USPC ..... Plt./247
CPC ..... A01H 5/00
See application file for complete search history.

*Primary Examiner* — Kent L Bell
(74) *Attorney, Agent, or Firm* — C. A. Whealy

(57) ABSTRACT

A new and distinct *Ilex* plant named 'FarrowSK6', characterized by its upright and narrowly pyramidal plant habit; freely branching habit; dense and bushy growth habit; small, glossy dark green-colored leaves; and good garden performance.

2 Drawing Sheets

Botanical designation: *Ilex crenata.*
Cultivar denomination: 'FarrowSK6'.

BACKGROUND OF THE INVENTION

The present Invention relates to a new and distinct *Ilex* plant, botanically known as *Ilex crenata* and hereinafter referred to by the name 'FarrowSK6'.

The new *Ilex* plant originated from an open-pollination during the spring of 1999 of *Ilex crenata* 'Sky Pencil', not patented, as the female, or seed, parent with an unknown selection of *Ilex crenata,* as the male, or pollen, parent. The new *Ilex* plant was discovered and selected by the Inventor during the summer of 2002 as a single plant within the progeny of the stated open-pollination in a controlled environment in Earleville, Md.

Asexual reproduction of the new *Ilex* plant by hardwood cuttings in Earleville, Md. since the autumn of 2002 has shown that the unique features of the new *Ilex* plant are stable and reproduced true to type in successive generations of asexual reproduction.

SUMMARY OF THE INVENTION

Plants of the new *Ilex* have not been observed under all possible environmental conditions and cultural practices. The phenotype may vary somewhat with variations in environmental conditions such as temperature and light intensity without, however, any variance in genotype. The following traits have been repeatedly observed and are determined to be the unique characteristics of 'FarrowSK6'. These characteristics in combination distinguish 'FarrowSK6' as a new and distinct *Ilex* plant:

1. Upright and narrowly pyramidal plant habit.
2. Freely branching habit; dense and bushy growth habit.
3. Small, glossy dark green-colored leaves.
4. Good garden performance.

Plants of the new *Ilex* differ from plants of the female parent, 'Sky Pencil', in the following characteristics:

1. Plants of the new *Ilex* are more pyramidal than and not as columnar as plants of 'Sky Pencil'.
2. Plants of the new *Ilex* have smaller and darker green-colored leaves than plants of 'Sky Pencil'.

Plants of the new *Ilex* can be compared to the plants of *Ilex crenata* 'Farrowone', disclosed in U.S. Plant Pat. No. 20,049. In side-by-side comparisons conducted in Grand Haven, Mich., plants of the new *Ilex* differed from plants of 'Farrowone' in the following characteristics:

1. Plants of the new *Ilex* were narrower than plants of 'Farrowone'.
2. Plants of the new *Ilex* were more freely branching than plants of 'Farrowone'.
3. Plants of the new *Ilex* had smaller and darker green-colored leaves than plants of 'Farrowone'.

BRIEF DESCRIPTION OF THE PHOTOGRAPHS

The accompanying colored photographs illustrate the overall appearance of the new *Ilex* plant. The photographs show the colors as true as it is reasonably possible to obtain in colored reproductions of this type. Colors in the photographs may differ slightly from the color values cited in the detailed botanical description, which accurately describe the colors of the new *Ilex* plant.

The photograph on the first sheet is a side perspective view of a typical plant of 'FarrowSK6'.

The photograph on the second sheet is a close-up view of typical stems and leaves of 'FarrowSK6'.

DETAILED BOTANICAL DESCRIPTION

The aforementioned photographs and following observations and measurements describe plants grown during the spring and summer in three-gallon containers in an outdoor nursery in Grand Haven, Mich. and under cultural practices typical of commercial production. Plants were four years old when the photographs and detailed description were taken. In the following description, color references are made to The Royal Horticultural Society Colour Chart, 1995 Edition, except where general terms of ordinary dictionary significance are used.

Botanical classification: *Ilex crenata* 'FarrowSK6'.

Parentage:

*Female, or seed, parent.*—*Ilex crenata* 'Sky Pencil', not patented.

*Male, or pollen, parent.*—Unknown selection of *Ilex crenata,* not patented.

Propagation:

*Type*.—By hardwood cuttings.

*Time to initiate roots, winter*.—About 40 days at temperatures of 20° C.

*Time to produce a rooted young plant, summer*.—About four months at temperatures of 20° C.

*Root description*.—Fine, fibrous.

*Rooting habit*.—Freely branching; dense.

Plant description:

*Plant and growth habit*.—Perennial shrub; upright and narrowly pyramidal plant habit; vigorous growth habit.

*Branching habit*.—Freely branching habit; dense and bushy growth habit with numerous lateral branches developing per plant.

*Plant height*.—About 150 cm.

*Plant diameter, area of spread*.—About 30 cm.

*Lateral branch description*.—Length: About 19 cm. Diameter: About 2.5 mm. Internode length: About 4 mm. Strength: Strong. Texture: Smooth, glabrous. Color: Close to 146A.

*Leaf description*.—Arrangement: Alternate, simple. Length: About 1.5 cm. Width: About 7 mm. Shape: Elliptical. Apex: Obtuse. Base: Obtuse. Margin: Mostly entire to slightly crenate. Venation pattern: Pinnate. Texture, upper and lower surfaces: Rugose, glabrous; glossy. Color: Developing leaves, upper surface: Close to 146B. Developing leaves, lower surface: Close to 146C. Fully expanded leaves, upper surface: Close to 147A; venation, close to 147A. Fully expanded leaves, lower surface: Close to 147B; venation, close to 147B. Petioles: Length: About 2 mm. Diameter: About 0.75 mm. Texture, upper and lower surfaces: Smooth, glabrous. Color, upper and lower surfaces: Close to 146B.

Flower description: Flower initiation and development has not been observed on plants of the new *Ilex*.

Garden performance: Plants of the new *Ilex* have been observed to have good garden performance and to be tolerant to rain, wind and temperatures ranging from about −20° C. to about 30° C.

Pathogen & pest resistance: Plants have not been observed to be resistant to pathogens and pests common to *Ilex*.

It is claimed:

1. A new and distinct *Ilex* plant named 'FarrowSK6' as illustrated and described.

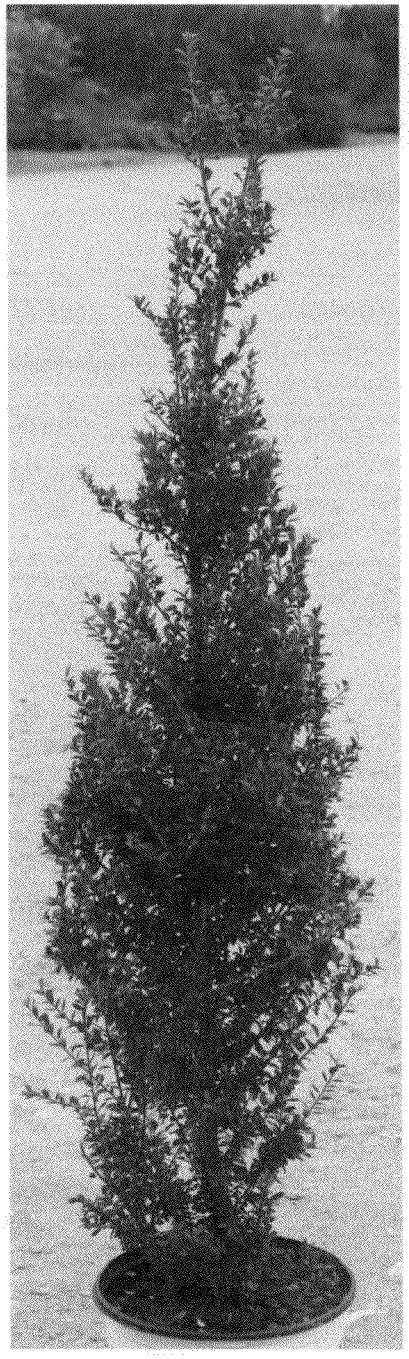

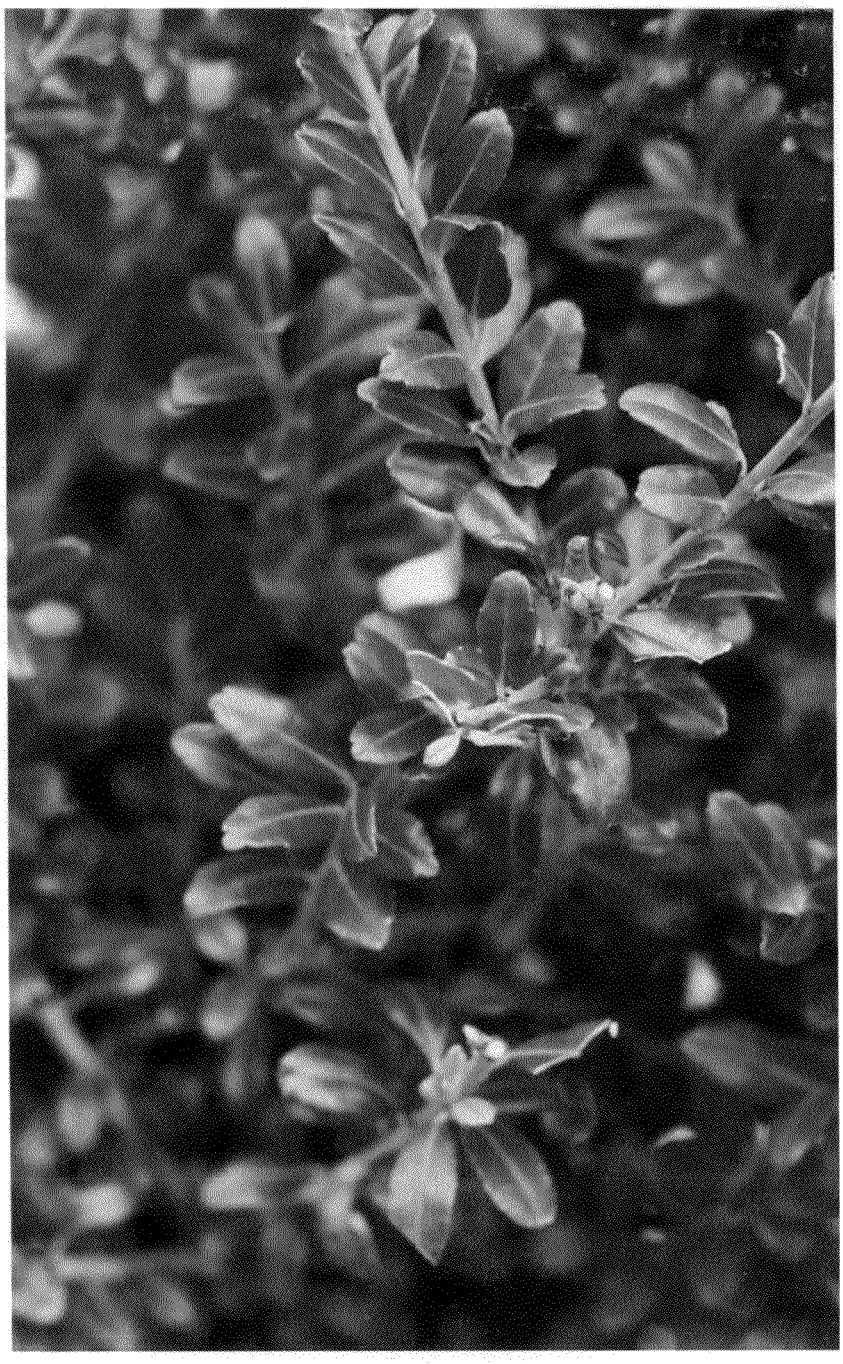

* * * * *